United States Patent

Weckström

[11] Patent Number: 5,908,789
[45] Date of Patent: Jun. 1, 1999

[54] ANALYSIS OF GAS MIXTURES WITH AN INFRARED METHOD

[75] Inventor: Kurt Peter Weckström, Espoo, Finland

[73] Assignee: Instrumentarium Oy, Helsinki, Finland

[21] Appl. No.: 08/815,831

[22] Filed: Mar. 12, 1997

[30] Foreign Application Priority Data

Mar. 14, 1996 [FI] Finland ..................................... 961197

[51] Int. Cl.⁶ ......................... G01N 33/00; G01N 21/01; G01N 21/31; G01N 21/35

[52] U.S. Cl. ......................... 436/133; 436/127; 436/134; 436/145; 436/164; 436/171; 250/339.12; 250/339.13; 250/343; 250/339.01; 250/339.06; 356/418; 356/435; 356/437; 422/82.09; 422/83

[58] Field of Search .......................... 250/339.12, 339.13, 250/343, 345, 339, 339.01, 339.02, 339.06, 339.07; 356/418, 435–440; 422/83, 82.09; 436/127, 133, 134, 145, 164, 171, 183

[56] References Cited

U.S. PATENT DOCUMENTS

| | | | |
|---|---|---|---|
| 3,790,798 | 2/1974 | Sternberg et al. | 250/345 |
| 3,832,548 | 8/1974 | Wallack | 250/343 |
| 3,968,367 | 7/1976 | Berg | 250/339.13 |
| 4,013,260 | 3/1977 | McClatchie et al. | 250/343 |
| 4,233,513 | 11/1980 | Elder et al. | 356/418 X |
| 4,567,366 | 1/1986 | Shinohara | 250/343 X |
| 4,891,518 | 1/1990 | Day | 250/343 |
| 4,914,719 | 4/1990 | Conlon et al. | 250/343 X |
| 5,081,998 | 1/1992 | Yelderman et al. | 250/339.13 X |
| 5,092,342 | 3/1992 | Hattendorff et al. | 250/343 X |
| 5,429,805 | 7/1995 | Uno et al. | 422/83 |
| 5,464,982 | 11/1995 | Drucker et al. | 250/345 X |
| 5,479,019 | 12/1995 | Gross | 250/345 |
| 5,486,699 | 1/1996 | Fabinski et al. | 250/345 |
| 5,610,400 | 3/1997 | Weckström | 250/345 |

FOREIGN PATENT DOCUMENTS

| | | |
|---|---|---|
| 307625 | 3/1989 | European Pat. Off. |
| 405841 | 1/1991 | European Pat. Off. |
| 53-042889 | 4/1978 | Japan |
| 1573641 | 8/1980 | United Kingdom |

Primary Examiner—Arlen Soderquist
Attorney, Agent, or Firm—Andrus, Sceales, Starke & Sawall

[57] ABSTRACT

The invention relates to a method and apparatus for determining the concentration of at least carbon dioxide in a gas mixture on the basis of the absorption of infrared radiation (2), said apparatus comprising: a radiation source (1), the radiation emitted thereby being aligned to travel through a measuring cell (4) containing a gas mixture (6) to be analyzed; an optical band-pass filter (10), which is transmissive to a first wavelength band and positioned on the path of radiation emerging from the measuring cell or entering into the measuring cell through which the radiation passes; and a first detector (14), positioned in the radiating direction downstream of said first band-pass filter and used for detecting the radiation intensity falling thereon. Said optical band-pass filter (10) has a band-pass which lies within the wavelength range of 4.38 $\mu$m–4.47 $\mu$m for measuring the total concentration of carbon dioxide by means of the absorption spectrum of a molecule $^{13}CO_2$ produced by a carbon isotope $^{13}C$.

33 Claims, 3 Drawing Sheets

ANALYSIS OF GAS MIXTURES WITH AN INFRARED METHOD

BACKGROUND OF THE INVENTION

The present invention relates to a method for analyzing the concentration of at least one component in a gas mixture on the basis of the absorption of infrared radiation, in which method: a radiation coining from a radiation source is allowed to pass through a gas mixture contained in a measuring cell, the absorption of at least said gas component to be measured having an effect on emerging radiation; the radiation going in or coming out of the measuring cell is allowed to pass trough an optical band pass filter transmissive at least to a certain first wavelength band; and the intensity of such filtered radiation is measured with a detector, which in the direction of radiation is positioned downstream of said first band pass filter and the measuring cell. Particularly, the invention relates to a measuring method based on infrared absorption for determining the concentration of carbon dioxide from a gas mixture, which most often also contains at least one other poorly absorbing gas component to be measured. The invention relates also to an apparatus for implementing the method.

The most common method of measuring carbon dioxide for example from alveolar air or an exhaust gas is to employ a measuring method based on non-dispersive infrared absorption. Carbon dioxide absorbs effectively over a range at 4.26 $\mu$m, and this is the range normally used since other gases do not generally have disturbing absorption there. If the concentration to be measured is about 10% by volume at normal pressure, a suitable absorbance in terms of measuring accuracy will be obtained over a measuring length, i.e. a distance traveled by radiation in a gas mixture, of 3–10 mm. If the carbon dioxide content is higher, the optimum measuring length will be even shorter. When, for some reason, it is necessary to use a longer measuring length, i.e. a thicker sample cell, the absorption will be so much deeper that measuring accuracy suffers. Such a condition arises if the same sample cell is to be used for measuring both a poorly absorbing gas component, e.g. alcohol, and carbon dioxide. This situation often leads to a compromise regarding the measuring length of a sample cell, whereby the absorbance of neither gas component is optimally selected. A very short sample cell is inconvenient for other technical reasons as well.

Several efforts to overcome this problem have been described in literature. The simplest approach is to use two separate series-connected sample cells having an unequal measuring length for carbon dioxide and poorly absorbing gas components, the short cell being used for measuring carbon dioxide and the long cell for measuring poorly absorbing components. In practice, however, such a solution is complicated and expensive, and in high-speed measuring there can be no certainty as to the duration and precision of a time lapse between various gas components.

The publication EP-309 666 discloses the use of a less powerful absorption range in the neighborhood of 2.7 $\mu$m. In principle, this would enable the use of a longer sample cell for measuring carbon dioxide but, as pointed out in the cited publication, water vapor absorbs in a disturbing manner over this range. Water vapor is present in substantial amounts in both alveolar air and for example in exhaust gas and, thus, the accurate measuring of carbon dioxide also requires the measuring of water vapor or the limination of its effect by some other means.

The spectral band of carbon dioxide over the range of 4.26 $\mu$m consists of a plurality of rotational lines. Near the beginning and end of the spectral band, the lines are less effectively absorbing, The restriction of measuring to cover just these weakly absorbing lines would in principle enable the measuring of carbon dioxide also by means of a sample cell having a long measuring length. However, the successful measuring requires the use of a highly narrow band and sensitive optical filter and, since the position of the passband of a filter in terms of its wavelength is very near the sharp edge of the spectral band, the produced signal will be highly temperature sensitive. Even a minor change in the temperature of any device component may offset the passband of the filter e.g. in the direction of the spectral band or beyond the sharp edge, at which the absorption of carbon dioxide increases dramatically.

The publication U.S. Pat. No. 5,429,805 discloses the use of an optical gas filter to limit away the most intensively absorbing spectral lines of a spectral band. The gas filter in series with a specimen cell contains the same or a similar gas as the gas to be measured, whereby the most intensively absorbing lines of this gas filter remove or reduce measuring radiation at said lines before the radiation reaches a detector. On the other hand, the more weakly absorbing Lines of the gas filter are only capable of removing very little radiation and, thus, the measuring can be effected over the wavelengths represented thereby, Hence, it is possible to employ a longer specimen or sample cell or to measure higher concentrations without developing deflecting non-linearity. The method is basically functional but the use of an optical gas filter is always inconvenient and expensive and, in addition, the leak hazard of a gas filter is also a considerable risk factor. It is also likely that the collision broadening caused by other components in a gas mixture to be analyzed has a disturbingly high impact upon the measuring signal of a component to be measured. The reason for this is that other components in a gas mixture to be analyzed may cause variable broadening of the absorption lines included in the spectral bands of a gas component to be measured while in a gas filter such broadening is not likely to occur at all, since the gas in a filter has a higher purity, or the broadening is at least constant since, in any case, the gas mixture in a filter remains unchanged. A consequence of this is that, as far as the absorption lines are concerned, the measuring result is affected more by the fringe than center sections of the lines and, in fact, the outcome may be that the measuring is more related to the collision broadening, i.e. the interaction of gas components, rather than to the concentration of a desired gas component.

BRIEF SUMMARY OF THE INVENTION

An object of the invention is to provide a method based on infrared absorption, which is capable of measuring even high carbon dioxide concentrations by using a sample or specimen cell, having a length which is sufficiently long in terms of practicality and measuring, accuracy. A second object of tie invention is to provide a method based on infrared absorption, whereby it is possible, over the same measuring length in a specimen cell, i.e. over the same passing distance of radiation through a gas mixture to be measured, to measure accurately and reliably both carbon dioxide and other gas components which require a long measuring length possibly as a result of weak absorption or a low concentration. Thus, the objective is to eliminate the need to use separate measuring cells for measuring various gas components and possible measuring errors resulting therefrom as well as to overcome other problems caused by a very short measuring cell length. A third object of the invention is to carry out the concentration measuring of carbon dioxide in such a manner that other components included in a gas mixture have as little impact as possible on the measuring result. A fourth object of the invention is to provide a simple and operatively reliable apparatus.

The above-described drawbacks can be eliminated and the above-defined objects are achieved by means of a method of the invention, which is characterized by what is set fort in the claims, and by means of a device of the invention, which is characterized by what is set forth in the claims.

The method and device of the invention make use of the absorption of carbon dioxide $^{13}CO_2$ produced by naturally occurring carbon isotope $^{13}C$ which is substantially weaker than the absorption of carbon dioxide $^{12}CO_2$ produced by the principal carbon isotope $^{12}C$, which is used in the prior known methods and devices.

A suitable point for measuring this isotope molecule is in the neighborhood of the wavelength range of 4.42 $\mu$m. Hereinbelow, the term isotope molecule refers to the carbon dioxide molecule $^{13}CO_2$, Furthermore, according to the invention, the concentration measuring result of this isotope molecule is used as a basis for calculating the total concentration of carbon dioxide. As the carbon dioxide concentration is thus determined by means of a weak absorption band, it is possible to determine the concentrations of also other components having a weak absorption band or components occurring in low concentrations by using a common specimen cell, i.e. a measuring cell, and, hence, approximately a common measuring length and to achieve a high measuring accuracy and measuring reliability. Likewise, a weak absorption band can be used for determining solely high concentrations of carbon dioxide by using a measuring cell, having a length which is sufficient for producing the other desired effects and for avoiding the problems.

BRIEF DESRIPTION OF THE SEVERAL VIEWS OF THE DRAWING

The invention will now be described in detail with reference made to the accompanying drawings.

DETAILED DESRIPTION OF THE INVENTION

Figure 1:
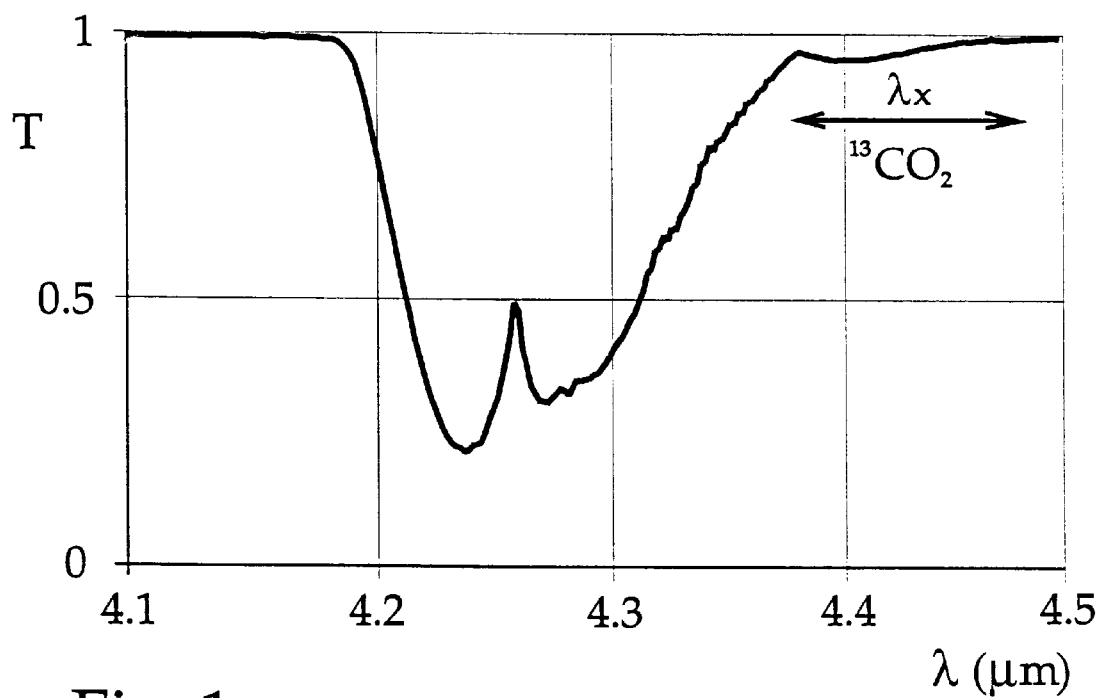
FIG. 1 illustrates an infrared spectrum for standard carbon dioxide $^{12}CO_2$ and for the respective isotope molecule $^{13}CO_2$ within a range preferred for the invention.
Figure 2:
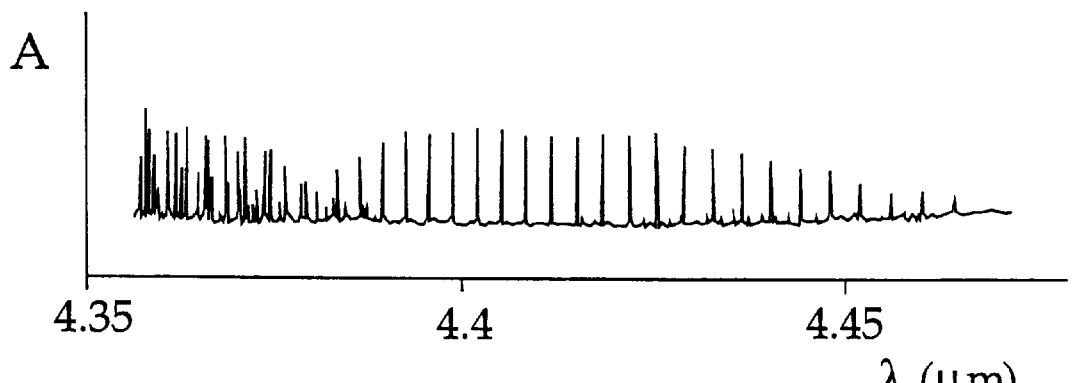
FIG. 2 shows in more detail an absorbance spectrum for the isotope molecule $^{13}CO_2$ over the range of 4.42 $\mu$m, depicting both an absorption band for the isotope molecule and absorption lines creating the band.

According to present knowledge, a naturally existing portion S of carbon isotope $^{13}C$ is 1.10%, while most of it is of standard type $^{12}C$. This indicates that also carbon containing molecules, such as carbon dioxide, have normally the same constant ratio of occurrence. As known in the art, when carbon dioxide produced by the main carbon isotope $^{12}C$ is measured over the range of 4.26 $\mu$m, the share of said isotope molecule is so insignificant that it is not easily even noticed in the spectrum. FIG. 1 depicts a transmission spectrum for carbon dioxide over the range of 4.1 $\mu$m–4.5 $\mu$m as measured with a resolution of 4 nm. Individual rotational lines are not visible as a result of poor resolution. The normal spectral band of carbon dioxide $^{12}CO_2$ lies within the range of 4.19–4.38 $\mu$m. To the right of this, FIG. 1 shows part of the spectrum of isotope molecule $^{13}CO_2$ clearly as a separate weak band. The range is visible more clearly with a resolution of 0.08 nm in FIG. 2, in whose absorbance spectrum also individual rotational lines are distinctly visible. The spectral band of molecule $^{13}CO_2$ has its central portion at a wavelength of 4.38 $\mu$m and, thus, the shorter wavelengths of the band are covered under the normal absorption of carbon dioxide. On the other hand, the spectrum has its P-branch within the range of 4.38 $\mu$m–4.47 $\mu$m and that is clearly visible and readily used for measuring. Since the occurrence rate S of isotope $^{13}C$ in relation to all carbon $\{^{13}C+^{12}C\}$ in nature is constant, i.e. about 1.10%, it is quite acceptable to use the infrared absorption produced by molecule $^{13}CO_2$ as a measure for the amount of carbon dioxide contained in an entire gas mixture, After the concentration of molecule $^{13}CO_2$ has been determined according to the invention by using the above-mentioned portion of an absorption band, the total carbon dioxide content is calculable by multiplying this measured value by an inverse value R of the above portion S of said naturally occurring isotope, which is within the range of 90–92. Thus, the total concentration of $CO_2$ is obtained mathematically. It is obvious that, in certain special conditions, the isotope ratios of carbon compounds included in a gas mixture to be measured can be other than the above naturally occurring ratio, whereby the ratio of $^{12}CO_2$ and $^{13}CO_2$ is also different. By no means does this preclude application of the invention, but only requires that the coefficient R used in computation be calculated to match the isotope ratio existing in a gas mixture to be measured.

It is easy to manufacture an optical filter having such a narrow passband $\lambda.x$, which can be used for accurately and reliably measuring the molecule $^{13}CO_2$ within the range of its absorption at 4.42 $\mu$m. Thus, the optical filter has its passband within the range of 4.38 $\mu$m–4.47 $\mu$m and it is optically structured as a conventional interference filter. If necessary, the passband can be made even narrower. Since absorption over this wavelength range of the invention is substantially lower than within the generally applied range of 4.19–4.38 $\mu$m, the passing distance of radiation through a gas mixture to be measured is according to the invention designed to be substantially longer than what it is when using this prior known wavelength band. In the measuring cell, a transmission length L of radiation is dimensioned to be so large that a low absorption of the spectral band of molecule $^{13}CO_2$ provides a high measuring accuracy over the carbon dioxide concentrations occurring during operation. Hence, in the inventive method and device, the transmission length L of radiation trough a sample gas is substantially longer than the length used for the same sample gas in a measuring process applying the molecule $^{12}CO_2$ of the principal carbon isotope or all isotope molecules, the optimum transmission length of radiation being at least five times or seven times, typically 10–100 times, preferably about 30 times longer than the optimum transmission length when measuring the same or a similar gas mixture by using the molecule $^{12}CO_2$. Thus, the same sample cell can also be used for accurately and reliably measuring other gas components of lesser absorption, such as alcohol existing in alveolar air or carbon monoxide existing in exhaust cases or hydrocarbons. In a measuring process of the invention, the absolute minimum transmission length L of radiation in a gas mixture to be measured is about 50 mm but, in practice, the minimum value is considered to be 70 mm. The optimal radiation transmission length L can be as long as 500 mm or even more but, from the viewpoint of cell dimensions and volume, it is often appropriate to use a some whatshorter length L, such as values within the range of 150 mm–300 mm. A typical length L is in the order of 200 mm.

The measuring apparatus can be arranged in a variety of ways. A few typical examples are shown in FIGS. 3–7. What these have in common is that the same sample cell can be used for measuring high carbon dioxide concentrations and other low-absorbing or low-concentration gas components or high carbon dioxide concentrations alone while achieving all the benefits described hereinbelow. Another reason why these above-type sample cells are preferred is that they can be readily used for restricting a beam of rays emerging from a radiation source to be sufficiently parallel, whereby an angle of incidence a of radiation relative to optical band-pass filters can be maintained small, in other words the radiation arrives at the filter or filters in a direction substantially perpendicular to the plane of the filter, This is necessary in order that the passband λx of an optical filter for molecule $^{13}CO_2$ and the pass-bands of other optical filters for other gas components to be analyzed be maintained during operation accurately to a planned width and at planned wavelengths. At the same time, however, the above type of sample cells are relatively small in terms of volume whereby, if necessary, it is possible to reliably monitor even rapid concentration changes in a gas mixture to be measured. The radiation source is typically a wide-band one, which means that the wavelength range radiated thereby has a width which exceeds the width of the passband λx of an optical band-pass filter. Preferably, the wavelength range radiated by the radiation source has such a width that the applied absorption bands of all gas components to be measured remain within the boundaries of radiation, the concentration of gas components being measurable by using the corresponding optical band-pass filters. In principle, it could be possible to employ corresponding narrow-band radiation sources and a detector provided with no band-pass filters, but this will lead to a complicated structure.

Figure 3:
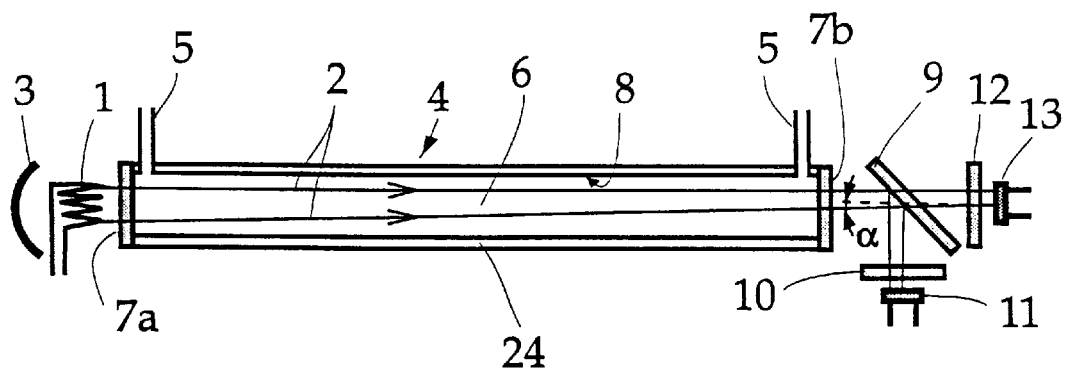
FIG. 3 shows a first embodiment for a measuring system of the invention, which employs a measuring method of the invention and in which the analyzing filters are disposed downstream of a specimen or sample cell in the advancing direction of measuring radiation.

In the embodiment of FIG. 3, a radiation 2 emitted by an infrared source 1 is sought to be maximized by means of optical components, such as a mirror 3, e.g. because of a long measuring distance. The radiation 2 is passed into a measuring or sample cell 4 provided with gas conduits 5 for picking up a gas sample 6. The sample cell 4 is elongated, preferably having a length of more than 100 mm e.g. for alcohol measurement. Both ends are provided with windows 7a and 7b transmissive to the applied radiation. The rays 2 passing through the sample cell may advance either directly without coming to contact with an inner surface 8 included in a housing 24 of said sample cell 4 or, depending on the sample cell length, said rays may reflect once or twice from the inner surface 8 of the cell housing. However, the radiation should have a distribution of the angle of incidence relative to optical band-pass filters 10 and 12 preferably no more than ±10°, i.e. the angle of incidence a must not exceed ±10°, for the employed narrow-band optical interference filters to function according to plan. In this embodiment, the radiation 2 divides in a beam splitter 9 in two portions for measuring various gas components. One of these is for measuring carbon dioxide as described above by means of the molecule $^{13}CO_2$. The band-pass filter 10 provided for this purpose has a band width which is preferably 1–2% of the average wavelength. The average wavelength should be about 4.42 μm. A detector 11 can either be made of lead selenide or it can be a thermal detector or some other detector sensitive over the relevant wavelength range. According to a particular application, the other measuring branch employs a suitable narrow-band filter 12 and a detector 13. The number of filter-detector assemblies can be more than two, if there are more gas components to be measured or if there is a need to use reference measuring at a wavelength having no infrared absorption. The angle of incidence on an optical filter can thus be provided as desired, even if the measurement would involve nothing but carbon dioxide.

Figure 4:
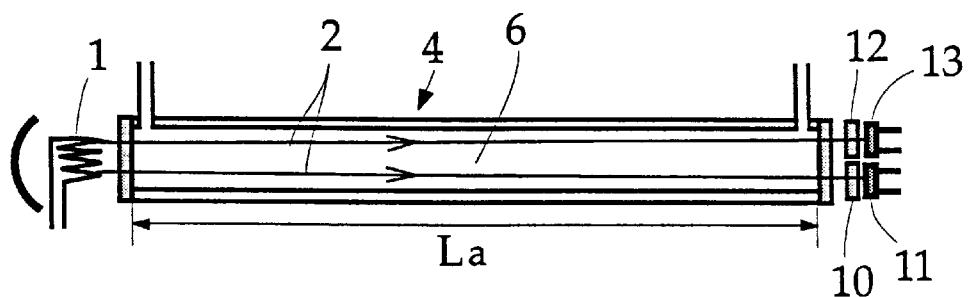
FIG. 4 shows a second embodiment for a measuring system of the invention, which employs a measuring method of the invention.

A measuring apparatus depicted in FIG. 4 is basically similar to that shown in FIG. 3 with the exception that there is no beam splitter. Downstream of a measuring and sample cell 4, the rays 2 fall directly on two filter-detector assemblies, of which a first assembly 10, 11 measures carbon dioxide as described by means of the molecule $^{13}CO_2$ and the other assembly 12, 13 measures some other gas component or is used for producing a reference value.

Figure 5:
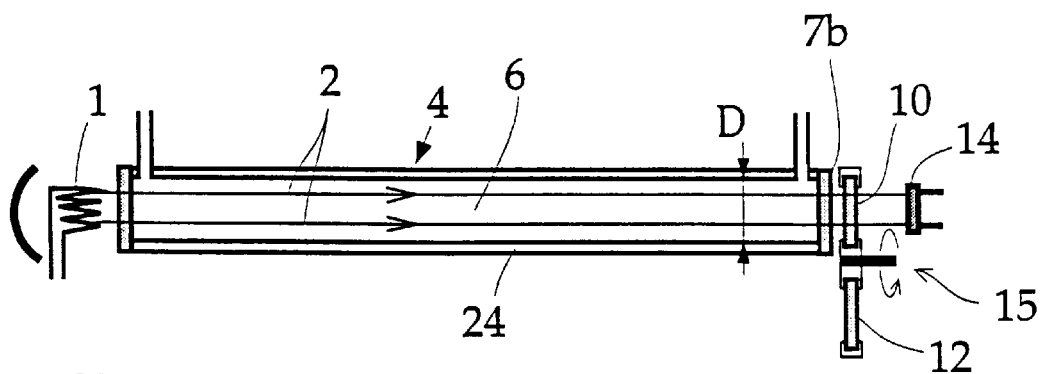
FIG. 5 shows a third embodiment for a measuring system of the invention, which employs a measuring method of the invention.

The embodiment of FIG. 5 employs just one detector 14. The band-pass filters 10 and 12 are included in a rotating disc 15 which positions each filter in turn on the path of radiation 2 between an output window 7b and the detector 14. If necessary, the disc 15 can be readily provided with more than two filters for measuring more than two gas components. In the embodiments of FIGS. 3–5 and 7, the measuring cell 4 comprises a tube, which is linear and in the advancing direction of radiation long relative to its inner diameter D, whereby a length La of the measuring cell between the radiation transmitting windows 7a and 7b thereof provides the radiation transmission length L. The cell 4 is provided with a housing 24 which is made of a solid material, having an index of refraction which exceeds that of a gas to be measured. The cell length La is adapted to be so large that the angular distribution of a beam of rays emerging through the output window 7b remains within the above-mentioned range of ±10°. Therefore, the cell length La is at least five times, but preferably 10–30 times more than the mean inner diameter of the cell. With this design, the rays, having an angle which differs substantially more than said about ±10° from the lengthwise direction of the tubes reflect several times from the inner surface 8 of the housing 24 of said cell 4 and, thus, become dampened and the portion represented thereby diminishes to an negligible level. Thus, such a measuring cell produces for the interference filters 10, 12 a sufficiently parallel beam of rays, even if the radiation source 1 were not an aligning one but, for example, would have a large surface area like the size of the tube diameter D or just slightly smaller than this diameter. This configuration has a benefit that the production of a nearly parallel beam of rays and a long radiation transmission length and a small cell capacity can be obtained without conflict by means of a small-diameter long cell.

Figure 6:
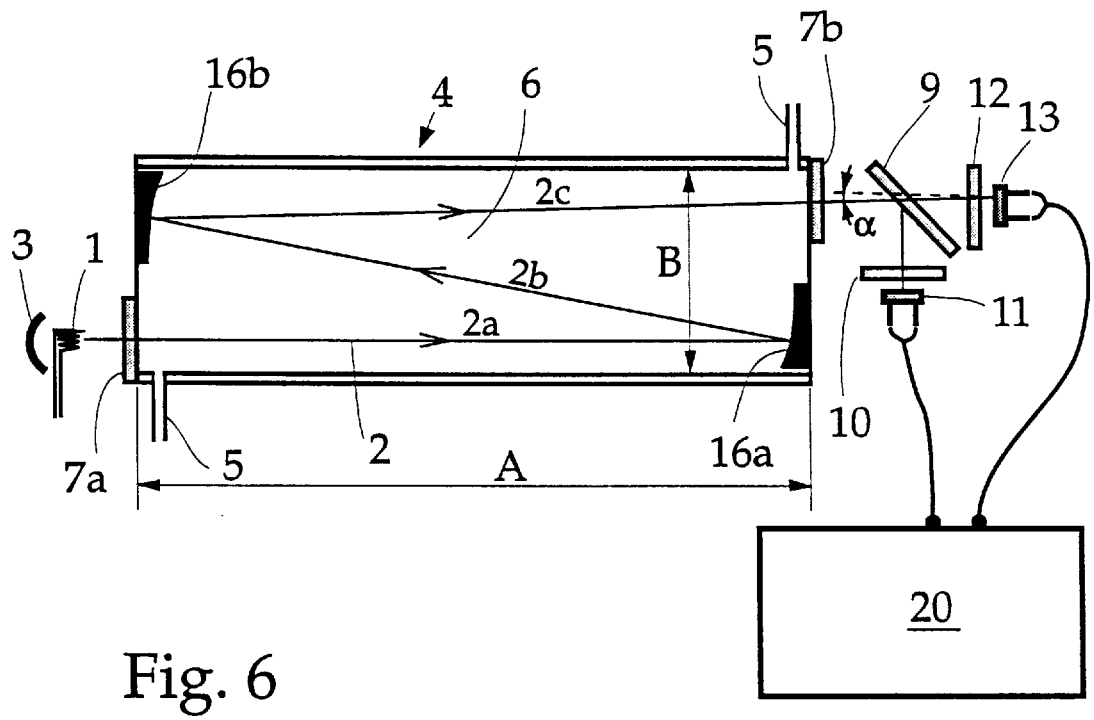
FIG. 6 shows a fourth embodiment for a measuring system of the invention, which employs a measuring method of the invention and in which the direction of measuring radiation is deflected within a specimen cell.

The embodiment of FIG. 6 is provided with a cell 4 having a relatively shorter length A and a relatively larger width B. Inside this cell are mounted mirrors 16a and 16b, which force a ray 2 to travel several times across the cell 4 in legs 2a, 2b and 2c. The sum of these legs Lb=2a+2b+2c provides an effective transmission length L for the ray 2. It is noted that, in this case, a mechanical cell length A is only about a third of the ray transmission length L=Lb. Of course, suitably curved mirrors or a number of further mirrors can be used for forcing the ray 2 to make even more legs across the cell, whereby the radiation transmission length L can be increased without having to substantially increase the external cell dimensions. In this case, the lateral cell dimension B is rather large relative to the diameter of the ray 2 and, thus, it is difficult to arrange the cell so as to achieve parallelism of the radiation. Hence, it is generally appropriate to provide a small surface-area or dot-like radiation source and/or to provide the radiation source with elements collimating its radiation, such that, as described above, the beam of rays arriving in the interference filters 10, 12 consists of nearly parallel rays, whose angle of incidence α is no more than about ±10°. The collimating elements may comprise not only a mirror 3 included in the radiation source but also the mirrors 16a, 16b, fitted inside the cell and reflecting the radiation 2. The radiation transmitting windows 7a, 7b can also be designed as radiation collimatings lenses. In this embodiment, the optical band-pass filters 10, 12 and detectors 11, 13 as well as a beam splitter 9 are included the same way as in the embodiment of FIG. 3. Also other filter-detector assemblies can be used in the association with the presently described measuring and sample cell 4.

Figure 7:
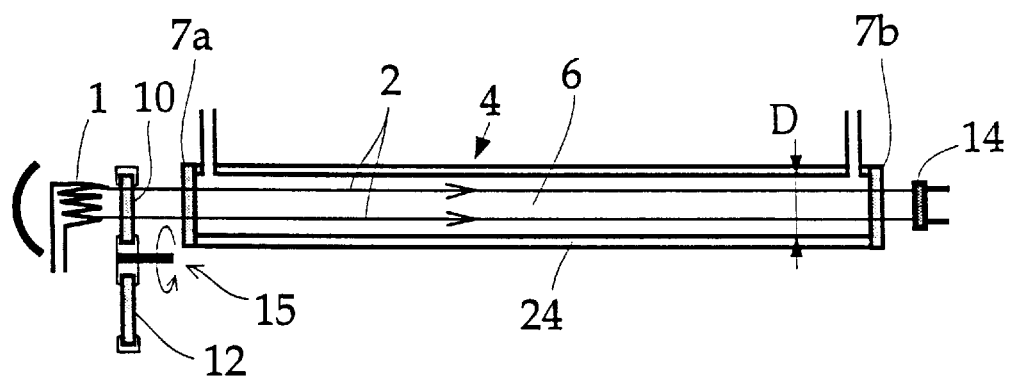
FIG. 7 shows a fifth embodiment for a measuring system of the invention, which employs a measuring method of the invention and in which the analyzing filters are disposed upstream of a specimen cell in the advancing direction of measuring radiation.

FIG. 7 depicts an embodiment of the invention, wherein the measuring or sample cell 4 is of the same type as in the embodiments of FIGS. 3–5 and the optical bandpass filters 10, 12 are of the same type and positioned the same way in a rotating disc 15. In this embodiment, however, the filters 10, 12 included in the disc are disposed between a radiation source 1 and an input window 7a of the cell 4, i.e. upstream of the cell in the radiation advancing direction. In this case the measuring cell is also designed, as described above, as a linear tube which is long relative to its inner diameter and such design limits the angle of incidence of the measurement-effecting radiation on the filter 10, 12 within the range of ±10°. This is based on the fact at, although in this case, some radiation from the radiation source 1 located near the optical band-pass filters in fact falls on the filters also at substantially larger angles of incidence, these rays which have reached the filter at a large angle of incidence come so many times in contact with the inner surface 8 of the housing 24 of said cell 4 that they dampen to a very small fraction of the original intensity thereof and, thus, shall have no influence on a signal produced by the detector. Hence, even in this case, the exploited radiation 2 has its angle of incidence on the optical band-pass filters within the above-described range so as to produce an approximately parallel beam of rays.

The apparatus of the invention is further provided with a calculator unit 20, as shown in the embodiment of FIG. 6 but included in one form or another in all embodiments, which effects the above-described multiplication with the inverse value R of a naturally occurring portion 1. 10% of the isotope $^{13}C$, which is thus within the range of 90–92. If the existing portion of isotope $^{13}C$ in the measuring cell in relation to all carbon isotopes put together is different from the above value, the inverse value R shall of course be worked out to correspond to this existing portion. Alternatively, the calculator unit 20 can be adapted to, output directly the total carbon dioxide content or a signal representative thereof, which is effected, for example, by linearizing and calibrating a signal received from the detector to correspond downstream of the calculator unit directly to the total concentration of carbon dioxide. Thus, it is not even necessary to know the proportional occurrences of various carbon isotopes, as long as they remain unchanged during calibration and the actual measuring processes. It is obvious that the apparatus includes other information processing units as well for processing the values provided by detectors. These units may be known as such and, thus, are not described further in his context The method and/or apparatus of the invention can be used for identifying and/or measuring not only carbon dioxide but also one, two or more other as components ill a gas mixture or solely carbon dioxide.

It is obvious that the infrared absorption of the isotope molecule $^{13}CO_2$ could be used as a quantity proportional to the infrared absorption of normal carbon dioxide also in other types of carbon dioxide measuring systems, not described above. For example, the use of a common sample tell for all gas components to be measured is the most preferred solution, but not absolutely necessary. The measurement of very high carbon dioxide concentrations by means of a molecule produced by the main isotope $^{12}C$ or by means of the co-action of molecules produced by all isotopes in a per se known manner would in practice require an unnecessarily short sample cell, which is why the system configuration is simpler and the measuring accuracy is higher if the measuring is effected on the molecule $^{13}CO_2$, even when there are no other gas components except carbon dioxide ($CO_2$). The same condition develops it for some other reason, it is not possible to use a short measuring length. It is obvious that the above-described method and apparatus of the invention can be used not only for measuring the concentration of some other gas component in addition to carbon dioxide but, if necessary, also for identifying the presence of some other gas component except carbon dioxide in a gas mixture.

I claim:

1. A method for analyzing gaseous components of a gas mixture by infrared radiation absorption, said method determining the concentration of a carbon dioxide gaseous component in the gas mixture, the total carbon dioxide component in the gas mixture being the sum of a larger fraction of carbon dioxide $^{12}CO_2$ containing the principal carbon isotope $^{12}C$ and a smaller fraction of carbon dioxide $^{13}CO_2$ containing the carbon isotope $^{13}C$, the quantitative relationship between the total carbon dioxide component and the amount of $^{13}CO_2$ contained therein being constant and being expressible in one or more formulations, the $^{12}CO_2$ being strongly absorbent of infrared radiation in a first spectral band, the $^{13}CO_2$ being weakly absorbent of infrared radiation in a second spectral band, said method further determining a characteristic of a second gaseous component of the gas mixture, said second gaseous component having weak infrared absorption properties generally resembling those of carbon dioxide $^{13}CO_2$, said method comprising the steps of:

providing a beam of infrared radiation;

passing the beam of infrared radiation through a sample of the gas mixture for absorption by the components of the gas mixture;

carrying out a first filtering step comprising filtering the beam of radiation to produce infrared radiation having wavelength properties which form the second spectral band, the second spectral band having wavelengths in a band of 4.38 μm to 4.47 μm and including the maximum absorption peak for $^{13}CO_2$;

measuring a property of infrared radiation so filtered after the radiation beam has passed through the sample, the measured property evincing radiation absorption by the $^{13}CO_2$ in the second spectral band;

determining, from the measurement, the concentration of the carbon dioxide gaseous component in the gas mixture using one of the formulations;

carrying out a second filtering step comprising filtering the beam of radiation to produce radiation having wavelength properties in a third spectral band selected in accordance with the infrared absorption properties of the second gaseous component; and measuring a property of the radiation filtered for the third spectral band after the radiation beam has passed through the sample to determine the characteristic of the second gaseous component from the absorption of the infrared radiation.

2. A method as set forth in claim 1 wherein the first filtering step is further defined as bandpass filtering the beam of radiation with a spectral passband centered at a wavelength of 4.42 μm.

3. A method as set forth in claim 1 wherein the determining step is further defined as determining the amount of $^{13}CO_2$ in the gas mixture and as using a formulation expressing the ratio of the $^{13}CO_2$ fraction to the total carbon dioxide component to determine the concentration of the carbon dioxide component in the gas mixture.

4. A method as set forth in claim 1 wherein the determining step is further defined as obtaining a signal proportional to the amount of $^{13}CO_2$ in the gas mixture and calibrating the signal in accordance with one of the formulations to produce an indication of carbon dioxide component concentration in the gas mixture.

5. A method as set forth in claim 1 wherein the step of passing the infrared radiation beam through the gas mixture is further defined as passing the radiation beam through a gas mixture sample contained in a sample cell, the optical length of which in a direction parallel to the passage of the radiation is selected in accordance with the generally similar weak absorption properties of $^{13}CO_2$ and the second gas.

6. A method as set forth in claim 1 wherein at least the first filtering step is carried out by applying infrared radiation to an optical interference filter and wherein the method includes the step of aligning the radiation of the radiation beam so that the radiation is applied to the optical interference filter at an angle of incidence not more than ±10° from a normal to the filter.

7. A method as set forth in claim 6 wherein the step of passing the infrared radiation beam through the gas mixture is further defined as passing the radiation beam through a gas mixture sample contained in a sample cell, wherein at least said first filtering step is further defined as filtering the radiation beam exiting the sample cell, and wherein the sample cell is so formed that the exiting radiation is aligned to provide the angle of incidence of not more than ±10° from a normal to the filter.

8. A method as set forth in claim 6 wherein the second filtering step is carried out by applying infrared radiation to an optical interference filter and wherein the method includes the step of aligning the radiation of the radiation beam so that the radiation is applied to the optical interference filter used in the second filtering step at an angle of incidence not more than +100 from a normal to the filter.

9. A method as set forth in claim 8 wherein the step of passing the infrared radiation beam through the gas mixture is further defined as passing the radiation beam through a sample contained in a sampling cell, wherein the second filtering step is further defined as filtering the radiation beam exiting the sample cell, and wherein the sample cell is so formed that the exiting radiation is aligned to provide the angle of incidence of not more than ±10° from a normal to the filter used in the second filtering step.

10. A method as set forth in claim 6 wherein the step of passing the beam of infrared radiation is further defined as passing the radiation through the gas mixture beam through a gas mixture sample cell in which the ratio of a dimension of the cell generally parallel to the direction of passage of the radiation beam and a dimension generally normal to the passage of the radiation beam is selected such that the exiting radiation is aligned at an angle of not more than ±10° to the direction of passage of the radiation beam.

11. A method as set forth in claim 1 wherein said method is further defined as one for determining the identity of the second gaseous component of the gas mixture.

12. A method as set forth in claim 1 wherein said method is further defined as determining the concentration of the second gaseous component in the gas mixture.

13. A method as set forth in claim 12 further defined as determining the concentration of a second gaseous component comprising alcohol in the gas mixture.

14. A method as set forth in claim 12 further defined as determining the concentration of a second gaseous component comprising carbon monoxide in the gas mixture.

15. A method as set forth in claim 1 wherein the first filtering step is carried out before the beam passes through the sample of the gas mixture.

16. Apparatus for analyzing gaseous components of a gas mixture by infrared radiation absorption, said apparatus determining the concentration of a carbon dioxide gaseous component in the gas mixture, the total carbon dioxide component in the gas mixture being the sum of a larger fraction of carbon dioxide $^{12}CO_2$ containing the principal carbon isotope $^{12}C$ and a smaller fraction of carbon dioxide $^{13}CO_2$ containing the carbon isotope $^{13}C$, the quantitative relationship between the total carbon dioxide component and the amount of $^{13}CO_2$ contained therein being constant and expressible in one or more formulations, the $^{12}CO_2$ being strongly absorbent of infrared radiation in a first spectral band, the $^{13}CO_2$ being weakly absorbent of infrared radiation in a second spectral band, said apparatus further determining a characteristic of a second gaseous component of the gas mixture, said second gaseous component having weak infrared absorption properties generally resembling those of carbon dioxide $^{13}CO_2$, said apparatus comprising:

an infrared radiation source providing a beam of infrared radiation along a radiation path;

a sample cell containing a sample of the gas mixture to be analyzed, said sample cell being inserted in said radiation path so that the beam of infrared radiation passes through the sample of the gas mixture for absorption by the components of the gas mixture;

a first optical interference bandpass filter inserted in said radiation path for filtering the radiation beam to produce infrared radiation having wavelength properties which form the second spectral band, said first optical interference bandpass filter having a passband of 4.38 μm to 4.47μm and including the maximum absorption peak for $^{13}CO_2$;

detector means positioned in the radiation path for receiving radiation filtered for said second spectral band after it has passed through said sample cell, said detector means detecting a property of the radiation evincing radiation absorption by the $^{13}CO_2$ in the second spectral band;

determining means for determining, from the property detected by said detector means, the concentration of the carbon dioxide gaseous component in the gas mixture using one of the formulations; and a second optical interference bandpass filter inserted in the radiation path for filtering the radiation beam to produce radiation having wavelength properties in a third spectral band selected in accordance with the infrared absorption properties of the second gaseous component;

said detector means being positioned in the radiation path for receiving radiation filtered for said third spectral bank after it has passed through said sample cell, said detector means detecting a property of the radiation evincing radiation absorption by the second gaseous component in the third spectral band;

said determining means determining from the detected property evincing radiation absorption by the second gaseous component in the third spectral band, the characteristic of the second gaseous component.

17. Apparatus as set forth in claim 16 wherein said first optical interference bandpass filter has a passband centered at a wavelength of 4.42 $\mu$m.

18. Apparatus as set forth in claim 16 wherein said determining means is further defined as means for determining the amount of $^{13}CO_2$ in the gas mixture and using a ratio of the $^{13}CO_2$ fraction to the total carbon component to determine the concentration of the carbon dioxide component in the gas mixture.

19. An apparatus as set forth in claim 16 wherein said detector means detects the amount of $^{13}CO_2$ in the gas mixture and provides a signal in accordance therewith, and wherein said determining means calibrates the signal in accordance with one of the formulations to produce an indication of carbon dioxide component concentration in the gas mixture.

20. Apparatus as set forth in claim 16 wherein said sampling cell has an optical length in a direction parallel to the passage of the radiation through the sample cell and wherein the optical length of said sampling cell is selected in accordance with the generally similar weak absorption properties of $^{13}CO_2$ and the second gas.

21. Apparatus as set forth in claim 20 wherein said sample cell includes mirror elements for increasing the optical length of the sample cell.

22. Apparatus as set forth in claim 16 wherein said first optical interference bandpass filter is inserted in said radiation path to receive radiation exiting from said sample cell and wherein said sample cell is so formed that the exiting radiation is aligned to provide an angle of incidence on said first optical interference bandpass filter of not more than ±10° from a normal to the filter.

23. Apparatus as set forth in claim 16 wherein said second optical interference bandpass filter is inserted in said radiation path to receive radiation exiting said sample cell and wherein said sample cell is so formed that the exiting radiation is aligned to provide an angle of incidence on said second optical interference bandpass filter of not more than ±10° from a normal to the filter.

24. Apparatus as set forth in claim 16 wherein said infrared radiation source includes collimating means for aligning the radiation of said beam so that said radiation is received on said first and second optical interference bandpass filters at an angle of incidence not more than ±10° from a normal to the filters.

25. Apparatus as set forth in claim 16 wherein said sample cell comprises a housing formed of a solid material having an index of refraction that exceeds that of the gas mixture, said sample cell having a first dimension generally parallel to the direction of passage of the radiation through the sample cell and a second dimension generally normal to the passage of the radiation, the ratio of said first dimension and said second dimension being selected such that the exiting radiation is aligned to provide an angle of incidence of not more than ±10° to the radiation path.

26. Apparatus as set forth in claim 16 including means for alternatingly inserting said first optical interference bandpass filter and said second optical interference bandpass filter in said radiation path.

27. Apparatus according to claim 16 wherein said detector means comprises first detector for receiving the radiation filtered for said second spectral band and second detector for receiving radiation filtered for said third spectral band.

28. Apparatus as set forth in claim 16 wherein said detector means comprises a common detector means for the radiation filtered for said second spectral band and the radiation filtered for said third spectral band.

29. Apparatus as set forth in claim 16 further defined as apparatus for determining the identity of the second gaseous component of the gas mixture.

30. Apparatus as set forth in claim 16 further defined as apparatus for determining the concentration of the second gaseous component in the gas mixture.

31. Apparatus as set forth in claim 30 further defined as apparatus for determining the concentration of a second gaseous component comprising alcohol in the gas mixture.

32. Apparatus as set forth in claim 30 further defined as apparatus for determining the concentration of a second gaseous component comprising carbon monoxide in the gas mixture.

33. Apparatus as set forth in claim 16 wherein said first optical interference bandpass filter is inserted in said radiation path intermediate said infrared radiation source and said sample cell.

* * * * *

UNITED STATES PATENT AND TRADEMARK OFFICE
CERTIFICATE OF CORRECTION

PATENT NO. : 5,908,789
DATED : June 1, 1999
INVENTOR(S) : Weckström

It is certified that error appears in the above-identified patent and that said Letters Patent is hereby corrected as shown below:

Claim 8, col. 9, line 61, delete "+100" and substitute therefor ---±10°---;
Claim 10, col. 10, line 5, after "radiation" insert ---through the gas mixture---; Claim 10, col. 10, line 6, delete "through the gas mixture---

Signed and Sealed this

Sixteenth Day of May, 2000

Q. TODD DICKINSON

*Attest:*

*Attesting Officer*          *Director of Patents and Trademarks*